United States Patent [19]
Goble et al.

[11] Patent Number: 5,397,356
[45] Date of Patent: Mar. 14, 1995

[54] PIN FOR SECURING A REPLACEMENT LIGAMENT TO A BONE

[75] Inventors: E. Marlowe Goble, Logan, Utah; Jerry L. Lower, Bourbon, Ind.

[73] Assignee: DePuy Inc., Warsaw, Ind.

[21] Appl. No.: 5,242

[22] Filed: Jan. 15, 1993

[51] Int. Cl.⁶ .............................................. A61F 2/08
[52] U.S. Cl. ...................................... 623/13; 606/73; 411/426
[58] Field of Search ....................... 606/73, 72, 60, 65; 411/426; 623/13, 18

[56] References Cited

U.S. PATENT DOCUMENTS

| | | | |
|---|---|---|---|
| 367,011 | 7/1887 | Rogers | 411/426 |
| 1,078,007 | 11/1913 | Stange | 411/426 |
| 2,382,019 | 8/1945 | Miller | 606/72 |
| 2,414,882 | 1/1947 | Longfellow | 606/73 |
| 4,738,255 | 4/1988 | Goble et al. | |
| 4,772,286 | 9/1988 | Goble et al. | 623/13 |
| 4,901,711 | 2/1990 | Goble et al. | 606/98 |
| 4,950,270 | 8/1990 | Bowman et al. | 606/72 |
| 4,952,213 | 8/1990 | Bowman et al. | 606/79 |
| 4,985,032 | 1/1991 | Goble | 606/96 |
| 5,013,316 | 5/1991 | Goble et al. | 606/72 |
| 5,019,078 | 5/1991 | Perren et al. | 606/61 |
| 5,067,962 | 11/1991 | Campbell et al. | 623/13 |
| 5,112,337 | 5/1992 | Paulos et al. | 606/96 |
| 5,234,301 | 8/1993 | Grossberndt et al. | 411/426 |

FOREIGN PATENT DOCUMENTS 1229452 4/1971 United Kingdom ................ 411/426

OTHER PUBLICATIONS

M. Kurosaka, "Crucial Choice for Winning Results", DePuy®, 1989, six pages.

Primary Examiner—Tamara L. Graysay
Attorney, Agent, or Firm—Barnes & Thornburg

[57] ABSTRACT

A pin is provided for securing a replacement ligament inside a tunnel of a receptor bone. The pin includes a body portion having a threaded section for engaging the receptor bone to anchor the pin in the receptor bone. The body portion also includes a tapered shank located adjacent the threaded portion. The tapered shank is configured to enter a drilled hole having a predetermined diameter formed in the replacement ligament to force the replacement ligament against the wall of the tunnel. The tapered shank has a first diameter at a first end of the tapered shank opposite the threaded portion which is smaller than the predetermined diameter of the drilled hole and a second diameter adjacent the threaded portion which is larger than the predetermined diameter so that the tapered shank engages the replacement ligament in the tunnel as the pin is inserted through the drilled hole in the replacement ligament to force the replacement ligament against a side wall of the tunnel to promote healing of the replacement ligament within the receptor bone. The pin further includes a head coupled to an end of the body portion adjacent the threaded section for driving the pin into the receptor bone.

21 Claims, 1 Drawing Sheet

PIN FOR SECURING A REPLACEMENT LIGAMENT TO A BONE

BACKGROUND AND SUMMARY OF THE INVENTION

This application relates to a pin for anchoring a replacement ligament inside a tunnel formed in a bone. More particularly, the present invention relates to a pin which facilitates securing a replacement ligament graft inside a bone and which promotes healing of the ligament graft inside the bone.

When a ligament such as an anterior cruciate ligament (ACL) of a knee is damaged or torn, a replacement ligament is often installed in the knee to reconstruct the natural anterior cruciate ligament. During such reconstruction, a tunnel is typically drilled through the anterior portion of the tibia upwardly through the tibial plateau and into the distal end of the femur to approximate the natural position of the anterior cruciate ligament. A bone-ligament-bone graft is then harvested, often from the patellar tendon following standard grafting procedures. Typically a wedge-shaped graft is cut and contoured using a graft guide. Sutural holes are then formed in the graft. The graft is then installed into the drill tunnel.

Various methods are known for securing the graft within the tibia and femur until the graft can heal. One such method is the use of a Kurosaka TM fixation screw. The Kurosaka TM screw provides an interference fit inside the tunnel with the graft so that the graft is wedged against the wall of the tunnel. See, for example, U.S. Pat. No. 4,950,270.

In other known methods, sutures coupled to the graft are anchored to the bone using screws or washers. The ligaments can also be coupled directly to the bone using plates or washers.

In addition, it is known to use a pin transverse to the drill tunnel to secure the graft within the tunnel. Various apparatus and methods are known for aligning the pin transverse with the drill tunnel to secure the ligament replacement to the bone. See, for example, U.S. Pat. No. 4,901,711 and U.S. Pat. No. 4,985,032.

Other methods and apparatus for locating and installing a transverse pin for securing a replacement ligament to a bone are described pending in U.S. patent application Ser. No. 08/004,987, entitled METHOD FOR SECURING A LIGAMENT REPLACEMENT IN A BONE by inventors Goble and Lower, filed concurrently herewith, and pending U.S. patent application Ser. No. 08/004958, entitled DRILL GUIDE APPARATUS by inventors Goble and Lower, also filed concurrently herewith.

The pin of the present invention provides advantages over the prior transverse pins and screws. The pin includes a smooth shank which is preferably tapered to push the bone plug of the bone graft against one side of the tunnel to promote healing of the graft in the bone. This tapered shank constitutes means for pushing or urging a portion of a ligament replacement into a wall of the tunnel to promote healing and bonding. In addition, the smooth shank provides a surface over which a replacement ligament can be positioned or looped if such a replacement ligament is used.

The pin of the present invention includes a head spaced apart from a threaded section of the pin so that the head of the pin engages the cortical bone of the femur and prevents the head from being counter sunk into the femur. This permits easy location of the pin through the skin should it be required to remove the pin. The pin of the present invention is easily removable from the femur when compared with the Kurosaka TM interference screw discussed above. As discussed above, access to the pin of the present invention can be obtained without substantial invasion of the knee.

According to one aspect of the present invention, a pin is provided for securing a replacement ligament inside a tunnel of a receptor bone. The pin includes a body portion having a threaded section for engaging the receptor bone to anchor the pin in the receptor bone. The body portion also includes means for engaging the replacement ligament to force the replacement ligament against a side wall of the tunnel to secure the replacement ligament inside a tunnel and to promote healing of the ligament. The pin further includes a head coupled to an end of the body portion adjacent the threaded section for driving the pin into the receptor bone.

In the illustrated embodiment, the engaging means includes a tapered shank located adjacent the threaded portion. The tapered shank is configured to enter a drilled hole having a predetermined diameter formed in the replacement ligament to force the replacement ligament against the wall of the tunnel. The tapered shank has a first diameter at a first end of the tapered shank opposite the threaded portion which is smaller than the predetermined diameter of the drilled hole. The tapered shank has a second diameter adjacent the threaded portion which is larger than the predetermined diameter so that the tapered shank engages the replacement ligament in the tunnel as the pin is inserted through the drilled hole in the replacement ligament to force the replacement ligament against a side wall of the tunnel to promote healing of the replacement ligament within the receptor bone.

Also in the illustrated embodiment, the pin includes a generally conical tip located on a opposite end of the body portion from the head. The generally conical tip is illustratively angled at an angle at about 30°.

The illustrated embodiment further includes a generally smooth neck located between the head and the threaded section of the body portion. The neck facilitates removal of the pin from the bone. The head is an external hex head to reduce the likelihood that the head will be buried in the receptor bone when the pin is installed into the receptor bone.

Additional objects, features, and advantages of the invention will become apparent to those skilled in the art upon consideration of the following detailed description of a preferred embodiment exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
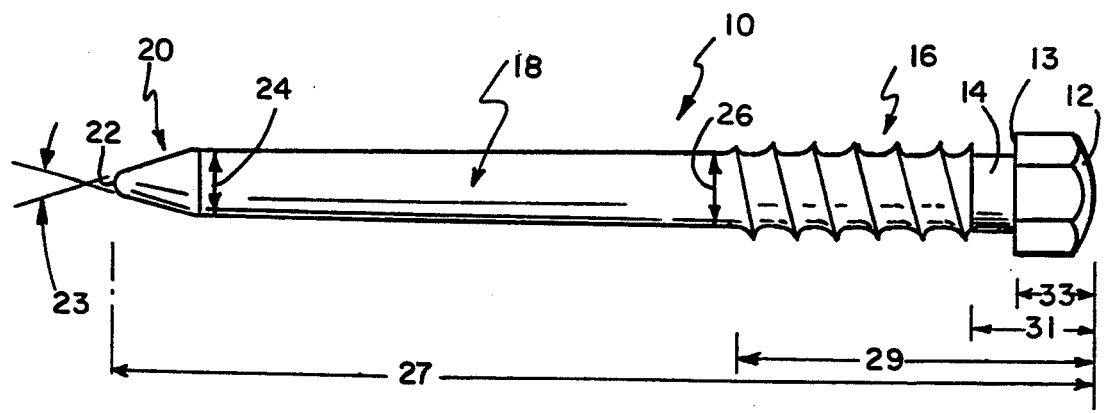
FIG. 1 is an elevational view of a pin of the present invention for securing or anchoring a replacement ligament inside a drill tunnel formed in a bone.
Figure 1A:
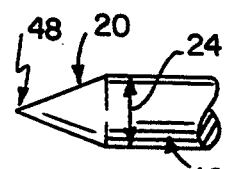
FIG. 1A shows a modification of the pin of FIG. 1 wherein the point of the pin is sharpened.

Referring now to the drawings, FIG. 1 illustrates a pin 10 of the present invention. Pin 10 includes a head 12 having an inner edge 13, a neck 14 located adjacent head 12, a threaded portion 16, a generally smooth shank 18, and a generally conical tip 20 at its distal end. Tip 20 illustratively has a smooth tapered nose 22. Nose 22 is illustratively blunt, smooth, or non-sharpened so that it does not pierce into the bone graft as the pin is inserted. Tip 20 is illustratively a 30° cone as illustrated by angle 23. Tip 20 is shaped to guide pin 10 through a hole drilled through the bone and through a hole formed in the replacement ligament graft. In certain applications, the nose of conical tip 20 may be sharpened as shown at 48 in FIG. 1A so that the sharpened nose pierces into the bone on an opposite side of a bone tunnel from head 12 of pin 10.

The smooth shank 18 of pin 10 is preferably slightly tapered. Illustratively, the diameter of shank 18 near tip 20 illustrated by dimension 24 is about 0.092 inch. The base diameter of shank 18 adjacent threaded section 16 illustrated by dimension 26 is larger than dimension 24. Illustratively, dimension 26 is about 0.112 inch.

Pin 10 has a length illustrated by dimension 27 which varies depending upon size required to effectively secure the ligament replacement within the bone. Illustratively, the length illustrated by dimension 27 may be 35 mm, 40 mm, 45 mm, 50 mm, 55 mm, 60 mm, or another length as required by the application. For each of the lengths, the distance from the end of head 12 to the end of threaded section 16 adjacent shank 18 illustrated by dimension 29 is about 0.5 inch. The distance from the end of head 12 to the end of neck 14 adjacent threaded section 16 illustrated by dimension 31 is about 0.18 inch. The distance from the end of head 12 to the inner edge 13 of head 12 illustrated by dimension 33 is about 0.1 inch.

Head 12 is illustratively an external hex head. Hex head 12 is spaced apart from threaded section 16 by smooth neck 14. The external hex is preferred for head 12 over an Allen screw or a slotted head. The external hex head 12 reduces the likelihood that the head will be buried as pin 10 is driven into a bone. As the head 12 starts to bury, an external hex driver (not shown) pulls off head 12.

Figure 2:
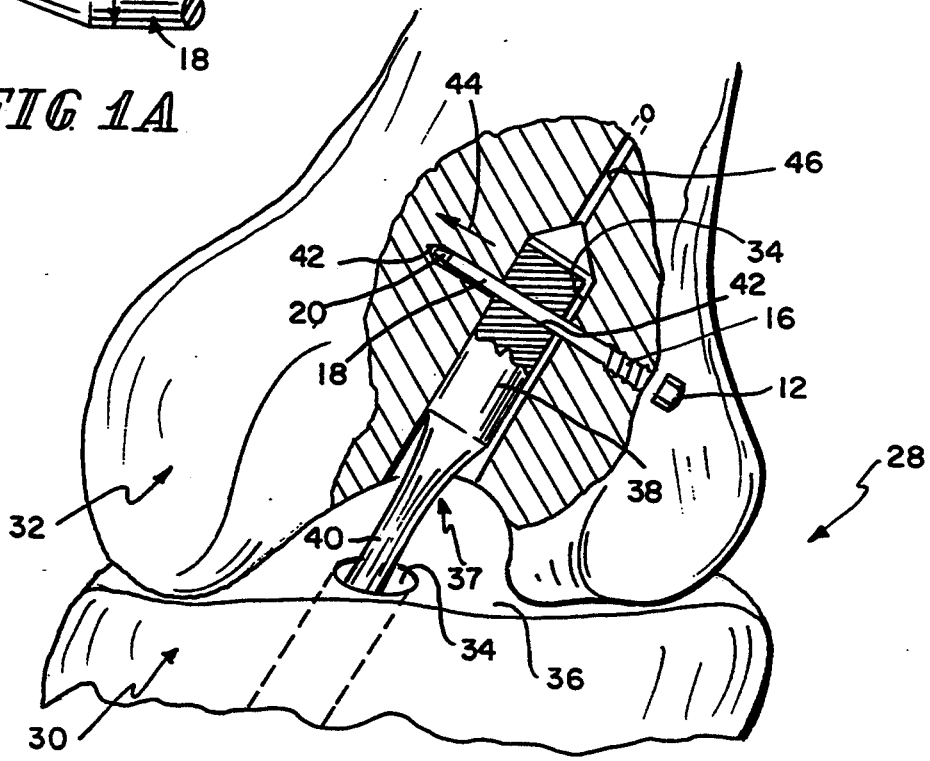
FIG. 2 is a diagrammatical view with portions broken away to illustrate the pin passing through the femur, through the tunnel in the bone, through the ligament replacement graft located in the tunnel and into the bone on an opposite side of the tunnel.

FIG. 2 illustrates pin 10 used to anchor a replacement anterior cruciate ligament in the femur of a knee joint. FIG. 2 illustrates a knee joint 28 including a tibia 30 and a femur 32. During replacement of the anterior cruciate ligament, a tunnel 34 is formed by drilling upwardly through the anterior surface of tibia 32, through tibial plateau 36, and into femur 32. Typically, the tunnel 34 is formed by passing a guide pin or K-wire along a desired path of the tunnel. The K-wire forms an aperture 46 through tibia 30 and femur 32. A cannulated drill (not shown) is then conventionally used to form the tunnel 34 by following the path of the K-wire.

After the tunnel 34 is formed in the bone, a replacement ligament is inserted into tunnel 34. In the FIG. 2 embodiment, the illustrative replacement ligament includes a harvested graft having a bony section or plug 38 and a ligament section 40. Another bony section or plug (not shown) is located in tunnel 34 inside tibia 30. A transverse guide hole 42 is then drilled through femur 32, tunnel 34, and bone graft 38. Guide hole 42 also extends into the portion of the femur 32 on an opposite side of tunnel 34.

Typically, guide hole 42 is formed with a drill having a diameter sized between dimension 24 and dimension 26 of smooth shank 18 of pin 10. Illustratively, the diameter of guide hole 42 is about 2.5 mm (0.0984 inch). Therefore, tip 20 and a portion of shank 18 adjacent tip 20 pass through the hole 42 in graft 38 without tightly engaging the wall defining hole 42. However, tapered shank 18 begins to engage the side wall defining guide hole 42 through graft 38 as the portion of tapered shank having a diameter larger than the diameter of hole 42 moves through hole 42 of graft 38. Therefore, tapered shank 18 of pin 10 applies a force normal to graft 38 in the direction of arrow 44 to force the graft against the wall of tunnel 34. By forcing graft 38 against the wall of tunnel 34, pin 10 secures graft 38 inside femur 32 and promotes healing and bonding of graft 38.

Smooth shank 18 of pin 10 bridges across tunnel 34. Therefore, pin 10 can also be used in the technique of looping a replacement ligament over pin 10 instead of the bone plug ligament graft illustrated in FIG. 2.

Threaded section 16 cuts into the bone of femur 32 to anchor pin 10 within femur 32. As discussed above, external hex head 12 reduces the likelihood that head 12 will be buried in femur 32. Edge 13 tends to engage the outer surface of femur 32. Head 12 is seated above the surface of femur 32. Therefore, hex head 12 can be located through the skin of a patient so that pin 10 can be rather easily removed upon healing or failure of the replacement ligament 37 through a small incision in the skin.

As pin 10 is removed from femur 32, threads 16 are backed out of femur 32. Once the end of threaded section 16 exits femur 32, pin 10 will simply spin upon rotation. Therefore, neck section 14 provides a region to permit pin 10 to be grasped and removed from femur 32 with a device similar to a nail puller (not shown).

Although the invention has been described in detail with reference to a certain preferred embodiment, variations and modifications exist within the scope and spirit of the invention as described and defined in the following claims.

What is claimed is:

1. A pin for securing a replacement ligament inside a tunnel of a receptor bone, the pin comprising:
a body portion including a threaded section for engaging the receptor bone to anchor the pin in the receptor bone, the body portion also including means for engaging and wedging the replacement ligament to force the replacement ligament against a side wall of the tunnel to secure the replacement ligament inside a tunnel and to promote healing of the ligament, the means for engaging and wedging having a smooth conical configuration with its larger circular cross section base facing toward the threaded section and its smaller circular cross section displaced further from the threaded portion than the base; the body also including a tapered tip portion at one end proximate to the means for engaging and wedging; and a head coupled to an end of the body portion adjacent the threaded section for driving the pin into the receptor bone.

2. The pin of claim 1, wherein the head is an external hex head to reduce the likelihood that the head will be buried in the receptor bone when the pin is installed into the receptor bone.

3. The pin of claim 1, wherein the tip portion is a sharpened tip formed on a second end of the body portion opposite from the head to pierce into a portion of the receptor bone on an opposite side of the tunnel from the head.

4. The pin of claim 1, wherein the tip portion is a generally conical tip and located on an opposite end of the body portion from the head.

5. The pin of claim 4, wherein the generally conical tip is angled at an angle at about 30°.

6. The pin of claim 1, further comprising a generally smooth neck located between the head and the threaded section of the body portion.

7. A pin for securing a replacement ligament inside a tunnel of a receptor bone, the pin comprising:

a body portion including a threaded section for engaging the receptor bone to anchor the pin in the receptor bone, the body portion also including means for engaging and wedging the replacement ligament to force the replacement ligament against a side wall of the tunnel to secure the replacement ligament inside a tunnel and to promote healing of the ligament, the body also including a tapered tip portion at one end proximate to the means for engaging and wedging; and a head coupled to an end of the body portion adjacent the threaded section for driving the pin into the receptor bone, wherein the means for engaging and wedging includes a tapered shank located adjacent the threaded portion, the tapered shank being configured to enter a drilled hole having a predetermined diameter formed in the replacement ligament to force the replacement ligament against the wall of the tunnel.

8. The pin of claim 7, wherein the tapered shank has a first diameter at a first end of the tapered shank opposite the threaded portion which is smaller than the predetermined diameter of the drilled hole and a second diameter adjacent the threaded portion which is larger than the predetermined diameter so that the tapered shank engages the replacement ligament in the tunnel as the pin is inserted through the drilled hole in the replacement ligament to force the replacement ligament against a side wall of the tunnel to promote healing of the replacement ligament within the receptor bone.

9. A pin for anchoring a replacement ligament in a tunnel formed in a receptor bone, the pin being inserted into a transverse hole drilled through the receptor bone, through the tunnel, through the replacement ligament located in the tunnel, and through a portion of the receptor bone on an opposite side of the tunnel, the drilled hole having a predetermined diameter, the pin comprising: a body portion, and a head portion formed on one end of the body portion for driving the pin into the receptor bone, the body portion including a tapered tip located at an opposite end of the body portion from the head, a generally smooth tapered shank located adjacent the tip and with its taper being different from the taper of the tip, a threaded portion located between the shank and the head for engaging the receptor bone to anchor the pin within the receptor bone, the tapered shank having a first diameter adjacent the tapered tip which is smaller than the predetermined diameter of the transverse hole and a second diameter adjacent the threaded portion which is larger than the predetermined diameter so that the tapered shank can engage the replacement ligament in the tunnel as the pin is inserted through the hole in the replacement ligament to force the replacement ligament against a side wall of the tunnel to promote healing of the replacement ligament within the receptor bone.

10. The pin of claim 9, wherein the tip of the body portion has a generally conical shape.

11. The pin of claim 10, wherein the generally conical tip is angled at an angle at about 30°.

12. The pin of claim 9, further comprising a generally smooth neck located between the head and the threaded section of the body portion.

13. The pin of claim 9, wherein the head is an external hex head to reduce the likelihood that the head will be buried in the receptor bone when the pin is installed into the receptor bone.

14. The pin of claim 9, wherein the tip is sharpened to pierce into a portion of the receptor bone on an opposite side of the tunnel from the head.

15. A pin for anchoring a bone or tissue graft in an opening of a receptor bone, said pin being provided for entering and extending through an exterior portion of the receptor bone and then through the opening and the graft, said pin having a proximal end to be located outside the receptor bone, a tapered distal end to be disposed inside the receptor bone, and an intermediate body portion, said pin also having a head portion disposed on said proximal end for engagement with a driving tool, a threaded portion adjacent said proximal end to engage the receptor bone, said intermediate portion being tapered downwardly in diameter from a point adjacent said threaded portion to a point adjacent said distal end and at a taper different from the distal end.

16. The pin of claim 15, wherein the pin further includes a reduced diameter portion between said threaded portion and said head portion.

17. The pin of claim 15, wherein the distal end of the pin has a generally conical shape.

18. The pin of claim 17, wherein the generally conical distal end is angled at an angle at about 30°.

19. The pin of claim 15, wherein the head is an external hex head to reduce the likelihood that the head will be buried in the receptor bone when the pin is installed into the receptor bone.

20. The pin of claim 15, further comprising a sharpened tip formed on the tapered distal end of the pin for piercing into a portion of the receptor bone on an opposite side of the opening from the head.

21. A pin for securing a replacement ligament inside a tunnel of a receptor bone, the pin comprising:

a body portion including a threaded section for engaging the receptor bone to anchor the pin in the receptor bone, the body portion also including means for engaging and wedging the replacement ligament to force the replacement ligament against a side wall of the tunnel to secure the replacement ligament inside a tunnel and to promote healing of the ligament, the engaging and wedging means having a smooth surface immediately abutting the threaded section, the body also including a tapered tip portion at one end proximate to the means for engaging and wedging; and a head coupled to an end of the body portion adjacent the threaded section for driving the pin into the receptor bone.

* * * * *